US009050373B2

(12) United States Patent
Lu et al.

(10) Patent No.: US 9,050,373 B2
(45) Date of Patent: Jun. 9, 2015

(54) PHARMACEUTICAL COMPOSITIONS COMPRISING ANTISENSE OLIGONUCLEOTIDES AND METHODS OF USING SAME

(75) Inventors: Qi Long Lu, Charlotte, NC (US); Bo Wu, Charlotte, NC (US)

(73) Assignee: The Charlotte-Mecklenburg Hospital Authority, Charlotte, NC (US)

( * ) Notice: Subject to any disclaimer, the term of this patent is extended or adjusted under 35 U.S.C. 154(b) by 30 days.

(21) Appl. No.: 12/800,376

(22) Filed: May 13, 2010

(65) Prior Publication Data

US 2011/0281787 A1 Nov. 17, 2011

(51) Int. Cl.
*C07H 21/04* (2006.01)
*C12N 15/11* (2006.01)
*A61K 47/48* (2006.01)

(52) U.S. Cl.
CPC ... *A61K 47/48315* (2013.01); *C12N 2310/3233* (2013.01); *A61K 47/48092* (2013.01); *A61K 47/4823* (2013.01); *A61K 47/48323* (2013.01)

(58) Field of Classification Search
CPC .............................................. C12N 2310/3233
See application file for complete search history.

(56) References Cited

U.S. PATENT DOCUMENTS

| | | | |
|---|---|---|---|
| 5,142,047 A | 8/1992 | Summerton et al. | |
| 6,124,271 A | 9/2000 | Iversen et al. | |
| 6,784,291 B2 | 8/2004 | Iversen et al. | |
| 7,049,431 B2 | 5/2006 | Iversen | |
| 7,468,418 B2 | 12/2008 | Iversen et al. | |
| 7,625,873 B2 | 12/2009 | Geller et al. | |
| 2008/0311040 A1* | 12/2008 | Berry et al. | 424/9.1 |
| 2010/0063133 A1 | 3/2010 | Neuman et al. | |

FOREIGN PATENT DOCUMENTS

| | | |
|---|---|---|
| WO | WO 2005/028617 A2 | 3/2005 |
| WO | WO 2005/116045 A1 | 12/2005 |
| WO | WO-2006/000057 A1 | 1/2006 |
| WO | WO 2006/020121 A1 | 2/2006 |
| WO | WO 2009/005793 A2 | 1/2009 |
| WO | WO 2009/070745 A1 | 6/2009 |
| WO | WO 2009070745 A1 * | 6/2009 |

OTHER PUBLICATIONS

Wu et al. (Molecular Therapy, 2009; 17(5):864-871).*
Wang et al. (Biotechnol Lett (2012) 34:19-28).*
Popplewell, L. J. et al., Molecular Therapy, 2009, vol. 17, pp. 554-561.*
Gabriel et al., "Morpholino Oligomers Targeting the PB1 and NP Genes Enhance the Survival of Mice Infected with Highly Pathogenic Influenza A H7N7 Virus," *Journal of General Virology*, vol. 89, 2008, pp. 939-948.
Jearawiriyapaisarn et al., "Sustained Dystrophin Expression Induced by Peptide-Conjugated Morpholino Oligomers in the Muscles of mdx Mice," *Molecular Therapy*, vol. 16, No. 9, Sep. 2008, pp. 1624-1629.
Warfield et al., "Gene-Specific Countermeasures Against Ebola Virus Based on Antisense Phosphorodiamidate Morpholino Oligomers," *PLoS Pathogens*, www.plospathogens.org, vol. 2, Issue 1, Jan. 2006, pp. 0005-0013.
Wells, Dominic J., "Peptide-Conjugated Antisense Therapy Takes a Skip Ahead," *Molecular Therapy*, vol. 16, No. 9, Sep. 2008, pp. 1523-1524.
Wu et al., "Dose-Dependent Restoration of Dystrophin Expression in Cardiac Muscle of Dystrophic Mice by Systemically Delivered Morpholino," *Gene Therapy*, vol. 17, 2010, published online Sep. 17, 2009, pp. 132-140.
International Search Report and Written Opinion for International Application No. PCT/US2011/034993, mailed Oct. 5, 2011.
Morcos, P.A.; "Achieving Efficient Delivery of Morpholino Oligos in Cultured Cells"; Genesis: The Journal of Genetics and Development; vol. 30; Issue 3; Jul. 2001; pp. 94-102.
Search Report for corresponding Chinese Patent Application No. 201180034226.8, dated Jan. 21, 2014.

* cited by examiner

*Primary Examiner* — Jon E Angell
(74) *Attorney, Agent, or Firm* — Alston & Bird LLP

(57) ABSTRACT

The invention provides compositions and associated methods for the antisense treatment of genetic disorders, infections and various other medical conditions. In particular, embodiments of the present invention are directed to pharmaceutical compositions comprising a combination of an antisense oligonucleotide compound conjugated with a positively charged polymer ("ON-PCP") and a negatively charged polymer. Pharmaceutical compositions in accordance with the present invention have demonstrated improved antisense efficiency and reductions in cell toxicity compared to compositions that contain an oligonucleotide compound conjugated with a positively charged polymer.

27 Claims, 3 Drawing Sheets
(2 of 3 Drawing Sheet(s) Filed in Color)

PHARMACEUTICAL COMPOSITIONS COMPRISING ANTISENSE OLIGONUCLEOTIDES AND METHODS OF USING SAME

BACKGROUND OF THE INVENTION

Antisense therapy is a promising form of treatment for genetic disorders, infections, and other disorders in which a strand of complimentary nucleic acid (DNA, RNA or a chemical analogue) is used to bind to a target sequence within an DNA or RNA strand, such as messenger RNA (mRNA), to thereby inactivate a targeted gene. Antisense therapy has also been used to restore gene function by inducing exon skipping in mutated genes.

Oligomers, including natural oligonucleotides and chemically modified oligomers, have shown particular potential in antisense therapy. Currently, oligomers are being studied for the treatment of cancers (including lung cancer, colorectal carcinoma, pancreatic carcinoma, malignant glioma and malignant melanoma), diabetes, ALS, Duchenne muscular dystrophy and diseases such as asthma and arthritis with an inflammatory component. Oligomers have also shown promise in the treatment of viral and bacterial infections.

Conjugating antisense oligonucleotide compounds with positively charged polymers has been shown to increase the effectiveness to which these molecules can be introduced into cells. However, conjugation with positively charged polymers has been associated with increases in toxicity. This is particularly problematic in cases where the effective therapeutic window of the antisense oligonucleotides lies close to the LD 50 dosage (dosage at which 50% of the experimental animals die). As a result, the use of antisense oligonucleotides has been limited.

Thus, there still exists a need for improved formulations for the administration of antisense oligonucleotides.

BRIEF SUMMARY OF THE INVENTION

The present invention provides compositions and associated methods for the antisense treatment of genetic disorders, infections and various other medical conditions. In particular, embodiments of the present invention are directed to pharmaceutical compositions comprising a combination of an antisense oligonucleotide compound conjugated with a positively charged polymer ("ON-PCP") and a negatively charged or amphiphilic polymer. Pharmaceutical compositions in accordance with the present invention have demonstrated improved antisense efficiency and reductions in cell toxicity compared to compositions that contain an oligonucleotide compound conjugated with a positively charged polymer. In one particular embodiment, the present invention is directed to a pharmaceutical composition comprising a combination of an antisense phosphorodiamidate morpholino oligomer (PMO) conjugated with a positively charged polymer ("PMO-PCP") and a negatively charged or amphiphilic polymer. Other antisense oligomers that may be used include peptide nucleic acid polymers (PNA).

It has been surprisingly discovered by the inventors of the present invention, that cell toxicity commonly associated with the treatment of oligonucleotides, and in particular PMO oligomers, that are conjugated with positively charged polymers is significantly reduced by combining the ON-PCP compounds with negatively charged polymers or amphiphilic polymers. It has also been unexpectedly discovered, that the efficiency of delivering the antisense oligonucleotide compounds, such as PMO oligomers, to the target RNA/DNA strand is improved by using the negatively charged polymers in combination with oligomer compounds conjugated with positively charged polymers. In general, it is commonly believed that the effectiveness of PMO-PCPs or PNA-PCP appears to be linked to the positive charges of the conjugated polymer, and the enhanced delivery is due to the binding of the positively charged polymer to the cell membrane. As such, conventional wisdom predicts that combining negatively charged polymers with ON-PCPs would result in neutralizing the enhancing effects of the positively charged polymers. Surprising, and contrary to expectations, the inventors discovered that by combining ON-PCPs with negatively charged polymers, cell toxicity can be reduced while still providing enhanced delivery of the antisense oligomer compounds to the cells. In some embodiments, it has been found that the combination of the negatively charged polymers and ON-PCPs can actually enhance the antisense effect.

Pharmaceutical formulations in accordance with the present invention can be used to treat a wide variety of medical conditions including bacterial and viral infections, cancers, diabetes, and genetic disorders, such as muscular dystrophy. In one embodiment, pharmaceutical formulations in accordance with the present invention can be used to treat viral infections such as Hepatitis B, Hepatitis C, Influenza virus, Ebola virus, and Marburg fever.

BRIEF DESCRIPTION OF THE SEVERAL VIEWS OF THE DRAWING(S)

The patent or application file contains at least one drawing executed in color. Copies of this patent or patent application publication with color drawing(s) will be provided by the Office upon request and payment of the necessary fee.

Having thus described the invention in general terms, reference will now be made to the accompanying drawings, which are not necessarily drawn to scale, and wherein:

FIG. 1 is a immunohistochemistry staining of muscle tissues of normal mouse (C57), control dystrophic mdx muscle (treated with scramble PPMO sequence not specific to the targeted dystrophin premRNA, second column from left) and mdx muscle treated with PPMO (third column from left) and mdx muscle treated with PPMO with formulation of DNA oligonucleotides (right column). The ratio of PPMO to DNA was 4:1. Red muscle fiber membrane staining in muscle tissues represents the dystrophin expression, which is absent in untreated mdx mice. The right column labeled as 30 mg/kg PPMO+DNA shows that the levels of dystrophin induction in different tissues are either the same as the tissues from mice treated with PPMO only, or clearly higher (in the heart) than the same tissue treated with PPMO only (the third column from left). Dystrophin protein is represented by the red membrane staining.

DETAILED DESCRIPTION OF THE INVENTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

The present invention provides compositions and associated methods for the antisense treatment of genetic disorders, infections and various other medical conditions. In particular, embodiments of the present invention are directed to pharmaceutical compositions comprising a combination of antisense oligonucleotide compounds conjugated with a positively charged polymer ("ON-PCP") and a negatively charged polymer or amphiphilic polymer. Pharmaceutical compositions in accordance with the present invention have demonstrated improved and antisense efficiency reductions in cell toxicity compared to compositions that contain an oligonucleotide compound conjugated with a positively charged polymer.

It has been surprisingly discovered by the inventors of the present invention, that cell toxicity commonly associated with the treatment of oligonucleotide compounds conjugated with positively charged polymers is significantly reduced by combining the ON-PCP compounds with negatively charged polymers. It has also been unexpectedly discovered, that the efficiency of delivering the oligonucleotide to the target RNA/DNA strand is improved by using the negatively charged polymers in combination with oligonucleotide compounds conjugated with positively charged polymers. In general, it is commonly believed that the effectiveness of ON-PCPs appears to be linked to the positive charges of the conjugated polymer, and the enhanced delivery is due to the binding of the positively charged polymer to the cell membrane. As such, conventional wisdom predicts that combining negatively charged polymers with ON-PCPs would result in neutralizing the enhancing effects of the positively charged polymers. Surprising, and contrary to expectations, the inventors discovered that by combining ON-PCPs with negatively charged polymers, cell toxicity can be reduced while still providing enhanced delivery of the antisense oligonucleotide compounds to the cells, especially in vivo and systemically. In some embodiments, it has been found that the combination of the negatively charged polymers and ON-PCPs can actually enhance the antisense effect.

Pharmaceutical formulations in accordance with the present invention can be used to treat a wide variety of medical conditions including bacterial and viral infections, cancers, diabetes, and genetic disorders, such as muscular dystrophy. In one embodiment, pharmaceutical formulations in accordance with the present invention can be used to treat viral infections such as Hepatitis B, Hepatitis C, Influenza virus, Ebola virus, and Marburg fever. Examples of bacteria that can be targeted in accordance with the present invention are described in U.S. Pat. No. 7,625,873.

The present invention can be used with a wide variety of antisense oligonucleotide compounds for use in antisense therapy. The terms "antisense oligonucleotide" and "antisense oligomer" are used interchangeably and refer to a sequence of nucleotide bases and a subunit-to-subunit backbone that allows the antisense oligomer to hybridize to a target nucleic acid (e.g., RNA/DNA) sequence by Watson-Crick base pairing, to form a nucleic acid:oligomer heteroduplex within the target sequence. Typically, such an oligomer is from 8 to about 50 nucleotide subunits long, and more typically about 12 to 25 nucleotide subunits long. The oligomer may have exact sequence complementarity to the target sequence or near complementarity.

In one embodiment, a preferred class of antisense oligonucleotide compounds for use in the present invention includes morpholino oligomers and peptide nucleic acids (PNA). Morpholino oligomers are polymeric molecules having a backbone which supports bases capable of hydrogen bonding to typical polynucleotides, wherein the polymer lacks a pentose sugar backbone moiety, and more specifically a ribose backbone linked by phosphodiester bonds which is typical of nucleotides and nucleosides, but instead contains a ring nitrogen with coupling through the ring nitrogen. Examples of suitable morpholino oligomers include phosphorodiamidate morpholino oligomer Examples of morpholino oligomers that may be used in the practice of the present invention are described in greater detail in U.S. Pat. Nos. 5,698,685, 5,217,866, 5,142,047, 5,034,506, 5,166,315, 5,185,444, 5,521,063, 5,506,337, 6,124,271, 6,784,291, 7,049,431, 7,582,615, and 7,625,873.

Peptide nucleic acid polymers (PNA) can also be used as antisense oligomers in the practice of the invention. PNA has the backbone structurally homomorphous with the deoxyribose backbone and consists of N-(2-aminoethyl)glycine units where the nucleobases are attached. PNA has been investigated as antisense oligomers for the potential of targeting genes related to human diseases. The easy synthesis of PNA together with positively charged polymers has lead PNA and its conjugates being widely tested as drugs of experimental therapy to cancers, genetic disorders and other diseases.

Oligonucleotide compounds, and in particular, morpholino oligomers and PNAs, can be conjugated with a wide variety of different positively charged polymers. Examples of positively charged polymers include peptides, such as argon rich peptides (Examples of positively charged peptides that may be used in the practice of the invention include R9F2C; $(RXR)_4$ XB (where X can be any amino acid); R5F2R4c; $(RFF)_3$; Tat proteins, such as TAT sequence CYGRKKRRQRRR; and (RFF)3R), cationic polymers, such as dendrimeric octaguanindine polymer, and other positively charged molecules as known in the art for conjugation to antisense oligonucleotide compounds. In one embodiment, the positively charged polymer comprises a polymer having a molecular weight that is from about 1,000 to 20,000 Daltons, and preferably from about 5,000 to 10,000 Daltons. Another example of positively charged polymers is polyethylenimine (PEI) with multiple positively charged amine groups in its branched or unbranched chains. PEI has else been widely used as gene and oligomer delivery vesicle.

Negatively charged polymers that can be used in the practice of the invention include negatively charged DNA, RNA oligonucleotides, peptides, and polysaccharides. Negatively charged oligonucleotides for used in the present invention typically have from about 2 to 1000 bases, and more typically from about 10 to 100 bases, with from about 15 to 50 bases being somewhat preferred, and from about 20 to 30 based being more preferred. In one embodiment, the negatively charged polymer comprises a peptide or polysaccharide having a molecular weight that is from about 1,000 to 20,000 Daltons, and preferably from about 5000 to 10000_Daltons.

Large negatively charged proteins, such as albumin may also be used for enhanced delivery and reduced toxicity with the ON-PCP compounds.

In a preferred embodiment, the negatively charge polymer comprises a negatively charged oligonucleotide having the same or similar sequence as the antisense oligonucleotide. Preferred oligonucleotides comprise DNA, RNA, or modified analogs thereof, such as 2'-O-methyl phosphorothioate oligonucleotides and 2'-O-methoxy-ethyl phosphorothioate oligonucleotides. In particular, the negatively charged polymers preferably comprise RNA, DNA, 2'-O-methyl phosphorothioate oligonucleotides, 2'-O-methoxy-ethyl phosphorothioate oligonucleotides, and combinations thereof that have the same or similar sequences as the administered antisense oligonucleotides so that negatively charge polymer targets the same target gene, target exons, or genetic target region of the gene that is targeted by the antisense oligonucleotides. Example of negatively charged polymers that can be used in the practice of the invention include 15 mer DNA oligonucleotide which can be used in formulation with PMO-PCP oligomers targeting mouse or human dystrophin sequences for exon skipping to treat Duchenne muscular dystrophy.

In a preferred embodiment, the invented formulation can use amphiphilic polymers such as pluronic copolymers. The nature of the polymers will neutralize the charge of PMO-PCP or PNA-PCP and enhance the delivery and reduce toxicity.

The ratio of the amount of the negatively charged oligonucleotide/polymer or amphiphilic polymers to the antisense oligonucleotide can range from about 1:100 to 100:1. In a preferred embodiment, the ratio of the amount of the negatively charged oligonucleotide/polymer or amphiphilic polymers to the antisense oligonucleotide is from about 0.2:1 to 1:5.

Pharmaceutical formulations comprising antisense oligonucleotides in accordance with the present invention may be administered in any convenient physiologically acceptable vehicle. Examples of standard pharmaceutically accepted carriers include saline, phosphate buffered saline (PBS), water, aqueous ethanol, emulsions such as oil/water emulsions, triglyceride emulsions, wetting agents, tablets and capsules. It should be recognized that the choice of suitable physiologically acceptable carrier will vary dependent upon the chosen mode of administration.

Pharmaceutical compositions in accordance with the present invention can be administered by treating a subject, such as a human, in need thereof with a therapeutically effective amount of the pharmaceutical formulation. In one embodiment, the pharmaceutical solution is provided in a solution that can be administered via intravenous injection to the subject. For example, a solution containing the pharmaceutical composition may be prepared by mixing a first solution containing the antisense oligonucleotide conjugated with a positively charged polymer with a second solution containing the negatively charged polymer. While not wishing to be limited by theory, it is believed in the inventive formulations the negatively charged polymers and ON-PCPs form an ionic complex via electrostatic attraction or hydrogen bonds between the negatively charged polymers and the positively charged polymers.

The pharmaceutical compositions of the present invention may be provided to target cells by any suitable means, including direct administration (e.g., in vitro by addition to culture medium, or in animals in vivo locally by injection or topical administration at a treatment site) or systemically (e.g., parenterally or orally). In one embodiment, the compounds and compositions comprise part of a physiologically acceptable solution so that in addition to delivery of the desired agent to the target cells, the solution does not otherwise adversely affect the electrolyte and/or volume and/or metabolism of the cells or tissue or subject.

The pharmaceutical compositions and compounds as utilized in this invention can be administered by intranasal, oral, inhalation, enteral, topical, intrauterine, vaginal, sublingual, rectal, intramuscular, intrapleural, intraventricular, intraperitoneal, ophthalmic, intravenous, or subcutaneous means. In a preferred embodiment, the pharmaceutical solution is provided via an intravenous injection.

Pharmaceutical compositions in accordance with the present invention may be supplied in liquid or solid form. Compositions in accordance with the present invention may further include solvents, diluents, excipients, preservatives, emulsifiers, compounds for adjusting odor, taste, pH or the like. In general, in addition to the active compounds, the pharmaceutical compositions of the invention may contain suitable excipients and auxiliaries which facilitate processing of the active compounds into preparations which can be used pharmaceutically. Suitable excipients include fillers such as sugars, for example, lactose, sucrose, mannitol or sorbitol, cellulose preparations, calcium phosphates, and binders such as starch, gelatin, methyl cellulose, hydroxypropyl methylcellulose, sodium carboxymethylcellulose, and/or polyvinyl pyrrolidone. If desired, disintegrating agents may be added, such as the above-mentioned starches as well as carboxymethyl starch, cross-linked polyvinyl pyrrolidone, agar, alginic acid, or a salt thereof. Auxiliaries include flow-regulating agents and lubricants, for example, silica, talc, stearic acid or salts thereof, and/or polyethylene glycol.

The formulations can be administered with or without additional carrier or diluent by the oral, systemic injections, percutaneous, transmucosal, or other typical route. Pharmaceutical formulations in accordance with the present invention may be administered orally in caplet, tablet, particle, granule, or powder forms.

The present invention also provides a method of treating and/or ameliorating the effects one or more medical conditions by administering a therapeutically effective amount and/or a prophylactic amount of the aforementioned pharmaceutical formulations, to a sufferer in need thereof. According to the present invention, a "therapeutically effective amount" of a compound, combination or pharmaceutical composition of the invention is an amount which is sufficient to achieve the desired pharmacological effect. Generally, the dosage required to provide an effective amount of the composition, and which can be adjusted by one of ordinary skill in the art, will vary, depending upon the age, health, physical condition, sex, weight and extent of disease, of the recipient. Additionally, the dosage may be determined by the frequency of treatment and the nature and scope of the desired effect.

As discussed above, the combination of the negatively charged polymers and/or amphiphilic polymers with antisense oligonucleotides conjugated with positively charged polymers allows higher dosages of the antisense oligonucleotide to be administered. Typical dosage amounts of the antisense oligomer in the pharmaceutical formulation may range from about 0.05 to 500 mg/kg body weight, and in particular from about 1 to 50 mg/kg body weight. In one embodiment, the dosage amount is from about 5 to 30 mg/kg body weight once or twice a week.

The dosage administered will, of course, vary depending on the use and known factors such as the pharmacodynamic characteristics of the active ingredient; age, health, and weight of the recipient; nature and extent of symptoms, kind of concurrent treatment, frequency of treatment, and the effect desired. The recipient may be any type of mammal, but is preferably a human. In one embodiment, dosage forms (compositions) of the inventive pharmaceutical composition may contain about 1 microgram to 1,000 micrograms of active ingredient per unit, and in particular, from about 2 to 80 micrograms of active ingredient per unit.

For intravenous delivery, a unit dose of the pharmaceutical formulation will generally contain from 0.05 to 200 micrograms per kg body weight and preferably will contain from 1 to 100 micrograms, in particular 10, 15, 20, 30, 40, 50, 60, 70, or 80 micrograms per kg body weight (μg/kg body weight) of the antisense oligomer. The pharmaceutical composition may be administered once or more times a day, or one or more times a week, for example 2, 3 or 4 times daily, or 2, 3 or 4 times weekly, and the total daily dose for a 70 kg adult will normally be in the range 10 to 700 micrograms. Preferred intravenous dosage ranges from 10 ng to 200 μg, preferably 2 to 200 μg, more preferably 10 to 100 μg of metal per kg of body weight. Alternatively the unit dose may contain from 2 to 20 micrograms of the antisense oligonucleotide and be administered in multiples, if desired, to give the preceding daily dose. In these pharmaceutical compositions, the antisense oligonucleotide will ordinarily be present in an amount of about 0.5-95% by weight based on the total weight of the composition.

In one particular embodiment, the inventive pharmaceutical compositions are particularly advantageously in the treatment of muscular disorders, such as Duchenne Muscular dystrophy (DMD). For example, in the use for the treatment of targeted muscle injuries or muscle related disorders, by way of general guidance, a daily oral dosage of the active ingredient (i.e., antisense oligonucleotide) can generally range from about 5 to 30 mg/kg of body weight when given on a weekly basis by intravenous injection. In a preferred embodiment, the antisense oligonucleotide can be administered at dosages of about 20 to 100 mg per kg of body weight when given once every 14 days by intravenous injection. It should be recognized that the dosage can be raised or lowered based on individual patient response. It will be appreciated that the actual amounts of antisense oligonucleotide used will vary according to the specific antisense oligonucleotide being utilized, the particular compositions formulated, the mode of application, and the particular site of administration.

For oral administration when the composition is in the form of a tablet or capsule, the active ingredient can be combined with an oral, non-toxic, pharmaceutically acceptable, inert carrier, including but not limited to, lactose, starch, sucrose, glucose, methyl cellulose, magnesium stearate, dicalcium phosphate, calcium sulfate, mannitol, sorbitol and the like. Additionally, when desired or necessary, suitable binders, lubricants, disintegrating agents, and coloring agents can also be incorporated into the mixture. Suitable binders may include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms may include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

In some embodiments, the nitrate ester formulations of the present invention may also be coupled with soluble polymers as targetable drug carriers. Such polymers can include, for example, polyvinylpyrrolidone, pyran copolymer, polyhydroxypropylmethacrylamide-phenol, polyhydroxyethylaspartamidephenol, or polyethyleneoxide-polylysine substituted with palmitoyl residues. In one embodiment, nitrate ester formulations in accordance with the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

The compositions described herein may be administered as part of a sustained-release formulation (i.e., a formulation such as a capsule or resin or sponge that effects a slow release of modulating agent following administration). Such formulations may generally be prepared using well known technology and administered by, for example, oral, rectal or subcutaneous implantation, or by implantation at the desired target site. Sustained-release formulations may contain a modulating agent dispersed in a carrier matrix and/or contained within a reservoir surrounded by a rate controlling membrane. Carriers for use within such formulations are biocompatible, and may also be biodegradable; preferably the formulation provides a relatively constant level of modulating agent release.

It is noted that humans are generally treated longer than mice or other experimental animals exemplified herein. Accordingly, the length of the treatment generally may be proportional to the length or intensity or prior duration of the disease or pathophysiological process, and may further depend on the animal species, drug effectiveness and degree of effect required or recommended. The doses may be single doses or multiple doses over a period of one to several days or longer.

In one embodiment, the pharmaceutical compositions and compounds of the present invention are administered topically, especially when the target of treatment includes areas or organs readily accessible by topical application, including diseases of the eye, the skin, or the lower intestinal tract. Topical application may also be readily used to administer the combinations, compounds and compositions of the invention to tissue below the skin, such as muscle. Suitable topical formulations may be prepared for each of these areas or organs.

Topical application for the lower intestinal tract may be effected in a rectal suppository formulation or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

Formulations suitable for topical administration to the eye also include eye drops wherein the active ingredients were dissolved or suspended in a suitable carrier, especially an aqueous solvent for the active ingredients. The active ingredients were preferably present in such formulations in a concentration of 0.5 to 20%, advantageously 0.5 to 10% and particularly about 1.5% w/w.

One can use topical administration to deliver a pharmaceutical formulation of the invention by percutaneous passage of the active agents into the systemic circulation of the patient. The skin sites include anatomic regions for transdermally administering the drug, such as the forearm, abdomen, chest, back, buttock, thigh and retroauricular area. The compound is administered to the skin by placing on the skin either a topical formulation comprising the compound or a transdermal drug delivery device that administers the compound. In either embodiment, the delivery vehicle is designed, shaped, sized, and adapted for easy placement and comfortable retention on the skin, or the formulation is applied directly on the skin in a prescribed amount and schedule.

Formulations suitable for topical administration include liquid or semi-liquid preparations suitable for penetration through the skin (e.g., liniments, lotions, ointments, creams, gels or pastes) and drops suitable for administration to the eye, ear, or nose. A suitable topical dose of active ingredient of a compound of the invention is 0.1 mg to 150 mg administered one to four, preferably one or two times daily. For topical administration, the antisense oligonucleotide may comprise from 0.001% to 10% w/w, e.g., from 1% to 2% by weight of the formulation, although it may comprise as much as 10% w/w, but not more than 5% w/w, or from 0.1% to 1% of the formulation.

When formulated in an ointment, the antisense oligonucleotides may be employed with either paraffinic or a water-miscible ointment base. Alternatively, the antisense oligonucleotides may be formulated in a cream with an emulsified cream base. If desired, the aqueous phase of the cream base may include, for example at Least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include methocarbamol, longer-chain alcohols, dimethylsulfoxide and related analogs.

A variety of transdermal drug delivery devices can be employed with the pharmaceutical formulations of this invention. For example, a simple adhesive patch comprising a backing material and an acrylate adhesive can be prepared. The drug and any penetration enhancer can be formulated into the adhesive casting solution. The adhesive casting solution can be cast directly onto the backing material or can be applied to the skin to form an adherent coating.

Transdermal administration may be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In other embodiments, the compound of the invention will be delivered using a liquid reservoir system drug delivery device. These systems typically comprise a backing material, a membrane, an acrylate based adhesive, and a release liner. The membrane is sealed to the backing to form a reservoir. The drug or compound and any vehicles, enhancers, stabilizers, gelling agents, and the like are then incorporated into the reservoir.

Matrix patches comprising a backing, a drug/penetration enhancer matrix, a membrane, and an adhesive can also be employed to deliver a compound of the invention transdermally. The matrix material typically will comprise a polyurethane foam. The drug, any enhancers, vehicles, stabilizers, and the like are combined with the foam precursors. The foam is allowed to cure to produce a tacky, elastomeric matrix which can be directly affixed to the backing material.

Also included within the invention are preparations for topical application to the skin comprising a compound of the invention, typically in concentrations in the range from about 0.001% to 10%, together with a non-toxic, pharmaceutically acceptable topical carrier. These topical preparations can be prepared by combining an active ingredient according to this invention with conventional pharmaceutical diluents and carriers commonly used in topical dry, liquid, and cream formulations. Ointment and creams may, for example, be formulated with an aqueous or oily base with the addition of suitable thickening and/or gelling agents. Such bases may include water and/or an oil, such as liquid paraffin or a vegetable oil, such as peanut oil or castor oil. Thickening agents that may be used according to the nature of the base include soft paraffin, aluminum stearate, cetostearyl alcohol, propylene glycol, polyethylene glycols, woolfat, hydrogenated lanolin, beeswax, and the like.

Lotions may be formulated with an aqueous or oily base and will, in general, also include one or more of the following: stabilizing agents, emulsifying agents, dispersing agents, suspending agents, thickening agents, coloring agents, flavouring agents, colouring agents, perfumes, and the like. Powders may be formed with the aid of any suitable powder base, e.g., talc, lactose, starch, and the like. Drops may be formulated with an aqueous base or non-aqueous base also comprising one or more dispersing agents, suspending agents, solubilizing agents, flavoring agents, coloring agents, and the like.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween™ 60, Span™ 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

The topical pharmaceutical compositions according to this invention may also include one or more preservatives or bacteriostatic agents, e.g., methyl hydroxybenzoate, propyl hydroxybenzoate, chlorocresol, benzalkonium chlorides, and the like. The topical pharmaceutical compositions also can contain other active ingredients such as antimicrobial agents, particularly antibiotics, anesthetics, analgesics, and antipruritic agents, as well as anti-fungal agents. Perfumes or volatile agents that confer an odour on the composition while, by evaporating, they 'set' or dry a topical formulation/application, may also be included.

The pharmaceutical compositions of the present invention can also be delivered through mucosal membranes. Transmucosal (i.e., sublingual, buccal, and vaginal) drug delivery provides for an efficient entry of active substances to systemic circulation and reduces immediate metabolism by the liver and intestinal wall flora. Transmucosal drug dosage forms (e.g., tablet, suppository, ointment, pessary, membrane, and powder) are typically held in contact with the mucosal membrane and disintegrate and/or dissolve rapidly to allow immediate systemic absorption.

In a related aspect, the present invention includes a method of treating or preventing a disease state by inhibiting or altering expression of a target protein. Such disease states include viral, bacterial or fungal infections, cancerous tumors, and other conditions characterized by cellular proliferation, such as restenosis, hyperproliferative skin disorders, or inflammation. Genes (at either DNA, RNA or protein levels) targeted, include transcription factors, which include many oncogenes, receptor proteins, matrix proteins, structural proteins and viral proteins. Inhibition of such proteins generally results in disruption of the cell cycle, viral replication, or other critical functions.

In one embodiment, the method is carried out by administering to the subject an antisense oligonucleotide, and in particular a morpholino oligomer that is selected to target a specific gene region aiming to restore specific gene expression or switch the isoforms of the gene. In general, the method comprises administering to a subject, in a suitable pharmaceutical carrier, an amount of the antisense agent effective to interfere with the integrety, transcription or splicing, and thus suppress or restore normal expression of the protein, or switch the expression of different isoforms. In a preferred embodiment, the method results in expression of a dominant negative variant of the protein. In one aspect of the method, the subject is a human subject. For use in antiviral treatment, various systemic routes of delivery, including oral and parenteral routes, e.g., intravenous, subcutaneous, intraperitoneal, and intramuscular, as well as inhalation, transdermal and topical delivery, can be used.

Typically, one or more doses of antisense oligonucleotide compounds are administered, generally at regular intervals, preferably once a day to once a month. Preferred doses for oral administration are from about 1 mg per kg of bodyweight oligomer to about 600 mg oligomer per kg body weight, and more preferably, from about 30 mg per kg of bodyweight oligomer to about 300 mg oligomer per kg body weight. For IV administration, the preferred doses are from about 0.1 mg per kg body weight to about 50 mg oligomer per kg body weight. Dosages will vary in accordance with such factors as the age, health, sex, size and weight of the patient, the route of administration, and the efficacy of the oligonucleotide agent with respect to the particular disease state. For treatment of infectious agents, a preferred dosage is typically that which is necessary to attain a concentration in the blood of from about 0.1 to about 10 µM, and more preferably about 400-1000 nM antisense oligomer. This concentration can be achieved in a variety of ways; doses of between about 1 and about 10 mg/kg/hour by continuous IV infusion have been found to be acceptable. Greater or lesser amounts of oligonucleotide may be administered as required.

An effective in vivo treatment regimen using the antisense oligonucleotides of the invention will vary according to the frequency and route of administration, as well as the condition of the subject under treatment. Optimum dosages for a given route can be determined by routine experimentation according to methods known in the art. Such in vivo therapy is generally monitored by tests appropriate to the particular type of ailment being treated, and a corresponding adjustment in the dose or treatment regimen can be made in order to achieve an optimal therapeutic outcome.

EXAMPLES

The toxicity of the inventive pharmaceutical formulations was explored. The results are summarized in TABLE 1 below. In this example, the toxicity of various dosage levels of PMO-PCP was compared to that of administering PMO-PCP in combination with a negatively charged polymer. In each of Trial Nos. 1 to 4, eight mice were injected once with a pharmaceutical composition comprising PMO-PCP. In Trials 3 and 4, the pharmaceutical composition also included a negatively charged polymer in addition to the PMO-PCP. The PMO-PCP is the antisense oligomers, E23+7-18, targeting the junction of exon 23 and intron 23 of mouse dystrophin and conjugated with the peptide of the $(RXRRBR)_2XB$ sequence (R=arginine, X=6-aminohexanoic acid and B=βalanine). The negatively charged polymer is the 15 mer DNA. In Trial No. 2, the dosage of PMO-PCP was at 120 mg/kg and resulted in all but one of the mice dyeing. In Trial No. 4 the same PMO-PCP dosage was used as in Trial No. 2. However, in Trial No. 4, the PMO-PCP composition was mixed with a negatively charged 15 mer DNA oligonucleotides. As can be seen in Table 1, only one out of 8 mice died with the same dose of PMO-PCP when the antisense oligomer was formulated with negatively charged DNA oligonucleotides in comparison to Trial No. 2. The ratio between the PMO-PCP and DNA is 4:1.

TABLE 1

| Trial No. | Treatment | PMO-PCP Dosage (mg/kg) | Total No. mice | Death after 2 weeks |
|---|---|---|---|---|
| 1 | PMO-PCP | 30 | 7 | 0 |
| 2 | PMO-PCP | 120 | 7 | 6 |
| 3 | PMO-PCP + DNA oligonucleotide | 30 | 8 | 0 |
| 4 | PMO-PCP + DNA oligonucleotide | 120 | 8 | 1 |

Figure 1:
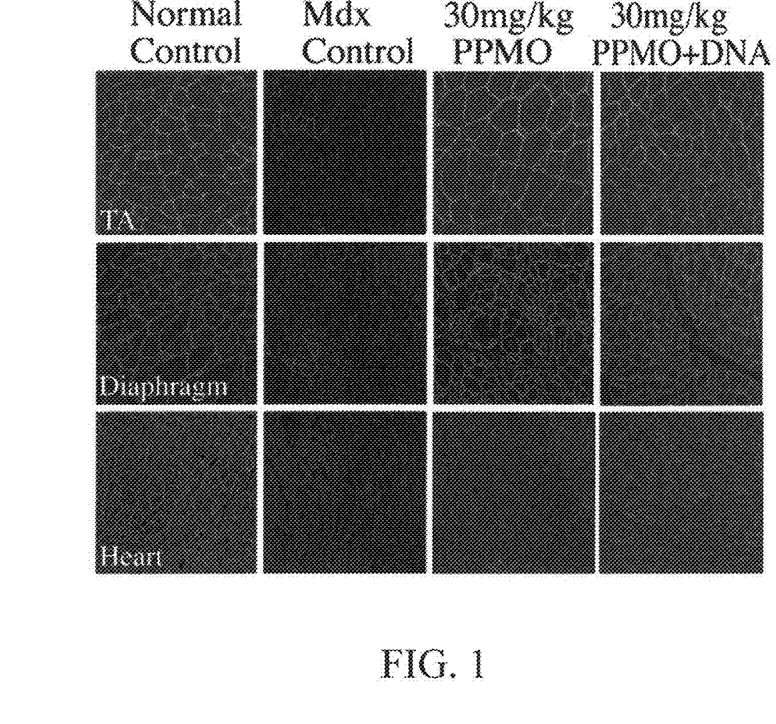

In this example, the effects of the inventive pharmaceutical composition in the treatment of dystrophic mice was compared to mice treated with phosphorodiamidate morpholino oligomer (PMO) conjugated with a positively charged peptide (PPMO). The PPMO in the inventive compositions were mixed with a negatively charged DNA oligomer comprising a 20 mer of DNA oligonucleotides. The ratio of PPMO to DAN was 4:1. The mice were treated with a single intravenous injection in which the dosage of PPMO was 30 mg/kg body weight. After 14 days, tissues samples were harvested for evaluation and staining. FIG. 1 is a immunohistochemical demonstration of dystrophin protein (red membrane staining) in muscle tissues of mdx mice treated with the PPMO/DNA oligomer formulation. Normal control tissues are from C57B110 mice; mdx control tissues are from mice treated with scramble PPMO sequence. The right column of FIG. 1 labeled as 30 mg/kgPPMO+ DNA shows that the levels of dystrophin induction in different tissues are either the same as the tissues from mice treated with PPMO only, or clearly higher (in the heart) than the same tissue treated with PPMO only (the third column from left). Dystrophin protein is represented by the red membrane staining with antibody specific to the dystrophin.

The examples of the above-discussed results demonstrate the effect of using negatively charged polymer or amphiphilic polymer for reducing toxicity significantly without affecting the efficacy of antisense oligomer. In fact, the results demonstrated the potential of enhancing the efficacy of antisense oligomer even via systemically delivery.

Figure 2:
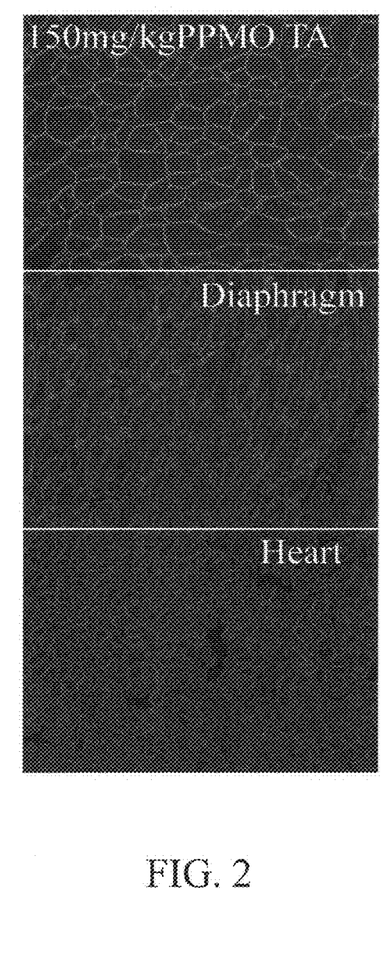
FIG. 2 is an image of immunohistochemical detection of dystrophin expression in the tissues of mdx mice after 120 mg/kg PPMO+DNA treatment. The strong red membrane staining indicates near normal levels of dystrophin in all muscles. Tissues are tested 2 weeks after the single i.v. injection of the PPMO/DNA formulation.

In the Example shown in FIG. 2, the effects of the inventive pharmaceutical composition on dystrophic muscle tissue was investigated. In particular, immunohistochemical detection of dystrophin expression in the tissues of mdx mice after 120 mg/kg PPMO+DNA (4:1) treatment was evaluated. In FIG. 2, the strong red membrane staining indicates near normal levels of dystrophin in all muscles. Tissues were tested 2 weeks after the single i.v. injection of the PPMO/DNA formulation. The results indicate that it becomes possible to use higher dose of PMO-PCP when such dosages are required to achieve therapeutic effect if the inventive formulation is used.

Figure 3:
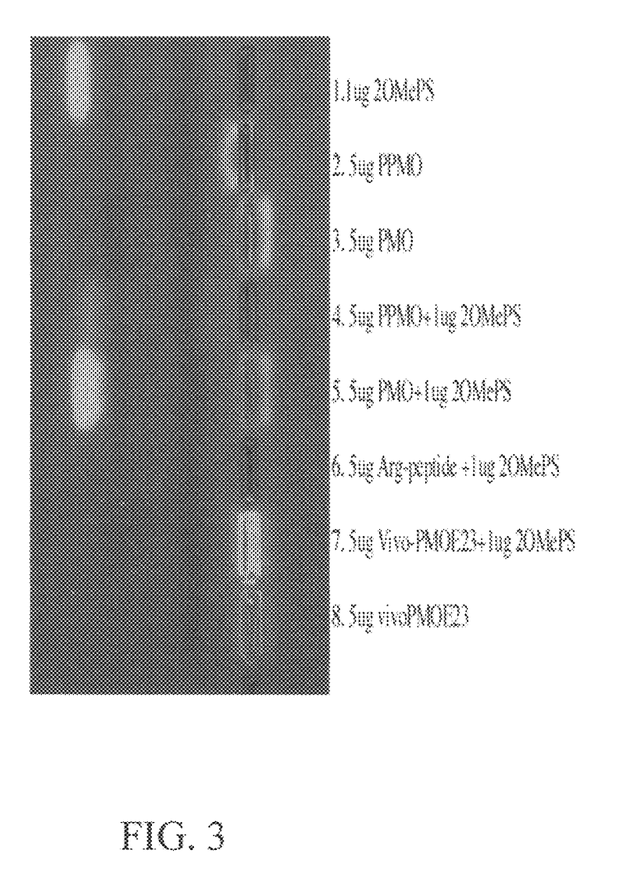
FIG. 3 is an agarose gel image comparing the binding of the negatively charged polymer to oligomers that have been conjugated with positively charged polypeptides. The image demonstrates the nucleic acid binding property of PPMO, VivoPMO and the Arginin-rich peptide (Arg peptide). VivoPMO binds most strongly to the 2O Methyl phosphorothioate RNA oligos (2OMePS). PMOE23 and PPMOE23 are the oligo sequences targeting mouse dystrophin exon 23. The Lower strong bands are ethidium bromide-stained 2OMePS oligos.

FIG. 3 is an agarose gel image that demonstrates the nucleic acid binding property of PPMO, VivoPMO and the Arginin-rich peptide (Arg peptide). VivoPMO binds most strongly to the 2O Methyl phosphorothioate RNA oligos (2OMePS). PMOE23 and PPMOE23 are the oligomer sequences targeting mouse dystrophin exon 23. The Lower strong bands are ethidium bromide-stained 2OMePS oligos.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A pharmaceutical composition comprising a mixture of an antisense oligonucleotide conjugated with a positively charged polymer, wherein the antisense oligonucleotide comprises a morpholino oligomer; and a negatively charged polymer, the composition when administered exhibits improved antisense efficiency and/or a reduction in cell toxicity in comparison to a composition containing the oligomer conjugated with a positively charged polymer.

2. The composition of claim 1, wherein the antisense oligonucleotide comprises a morpholino oligomer having from about 15 to 40 base pairing units (monomers).

3. The composition of claim 2, wherein the morpholino oligomer comprises a phosphorodiamidate-linked morpholino oligomer.

4. The composition of claim 1, wherein the positively charged polymer is a peptide.

5. The composition of claim 1, wherein the positively charged polymer is a cationic polymer.

6. The composition of claim 1, wherein the positively charged polymer is dendrimeric octaguanidine polymer.

7. The composition of claim 1, wherein the negatively charged polymer comprises an RNA or DNA strand having from about 2 to 50 base pairs.

8. The composition of claim 1, wherein the negatively charged polymer comprises a polysaccharide.

9. The composition of claim 1, wherein the negatively charged polymer comprises 2'-O-methyl phosphorothioate oligonucleotide.

10. The composition of claim 1, wherein the negatively charged polymer comprises 2'-O-methoxyethyl phosphorothioate oligonucleotide.

11. The composition of claim 1, wherein the negatively charged polymer is ionically bound to a positively charged polymer conjugated with the antisense oligonucleotide.

12. The composition of claim 1, wherein the ratio of the negatively charged polymer to the antisense oligomer conjugated with a positively charged polymer is from about 1:100 to 100:1.

13. The composition of claim 1, wherein the ratio of the negatively charged polymer to the antisense oligomer conjugated with a positively charged polymer is from about 0.2:1 to 1:5.

14. A pharmaceutical composition comprising
a phosphorodiamidate-linked morpholino oligomer conjugated with a positively charged polymer;
a negatively charged polymer; and
a carrier, the composition when administered exhibits improved antisense efficiency and/or a reduction in toxicity in comparison to a composition containing the oligomer conjugated with a positively charged polymer.

15. The pharmaceutical composition according to claim 14, wherein the antisense oligomer and the negatively charged polymer are both complimentary, near complimentary or non complimentary to a same target region of DNA or RNA.

16. The pharmaceutical composition according to claim 14, wherein the negatively charged polymer comprises 2'-O-methyl phosphorothioate oligonucleotide or 2'-O-methoxyethyl phosphorothioate oligonucleotide.

17. A method for treating a medical condition to a subject in need thereof comprising administering to a patient a therapeutically effective amount of a pharmaceutical composition comprising an antisense oligonucleotide conjugated with a positively charged polymer; and a negatively charged polymer, the composition when administered exhibits improved antisense efficiency and/or reduced toxicity in comparison to a composition containing the oligomer conjugated with a positively charged polymer.

18. The method of claim 17, wherein the antisense oligonucleotide comprises phosphorodiamidate-linked morpholino oligomer or a PNA oligomer.

19. The method of claim 17, wherein the positively charged polymer is a peptide, cationic polymer, or a combination thereof.

20. The method of claim 17, wherein a solution containing the negatively charged polymer is mixed with a solution containing the antisense oligonucleotide conjugated with a positively charged polymer prior to the step of administering the pharmaceutical composition.

21. The method of claim 17, wherein the medical condition is a bacterial or viral infection.

22. The method of claim 17, wherein the medical condition is cancer.

23. The method of claim 17, wherein the medical condition is a muscle related disease.

24. The method of claim 17, wherein the medical condition is a muscular dystrophy.

25. The method of claim 17, wherein the pharmaceutical composition is administered at a dosage from about 0.5 mg to 300 mg/kg body weight.

26. A pharmaceutical composition comprising a mixture of an antisense oligonucleotide conjugated with a positively charged polymer, wherein the antisense oligonucleotide comprises a morpholino oligomer; and a negatively charged polymer, the composition when administered exhibits improved antisense efficiency and/or reduced toxicity in comparison to a composition containing the oligomer conjugated with a positively charged polymer; and wherein the negatively charged polymer comprises the same or similar sequence as the antisense oligonucleotide.

27. A pharmaceutical composition of claim 26, wherein the negatively charged polymer is selected from the group consisting of RNA, DNA, 2'-O-methyl phosphorothioate oligonucleotides, 2'-O-methoxy-ethyl phosphorothioate oligonucleotides, and combinations thereof.

\* \* \* \* \*

UNITED STATES PATENT AND TRADEMARK OFFICE
CERTIFICATE OF CORRECTION

PATENT NO. : 9,050,373 B2
APPLICATION NO. : 12/800376
DATED : June 9, 2015
INVENTOR(S) : Lu et al.

It is certified that error appears in the above-identified patent and that said Letters Patent is hereby corrected as shown below:

On Title Page:
Item (73), Assignee: Please correct the Assignee to read as below:
   The Charlotte-Mecklenburg Hospital Authority D/B/A Carolinas Healthcare System
Charlotte, NC (US)

Item (74), Attorney, Agent, or Firm: Please correct attorney names to read as below:
   Myers, Bigel Sibley & Sajovec, P.A.

Specification:
Column 4, Lines 44-45: Please correct "R5F2R4c; (RFF)$_3$;"
   to read -- R5F2R4C; (RFF)3; --

Signed and Sealed this
Thirty-first Day of May, 2016

Michelle K. Lee
*Director of the United States Patent and Trademark Office*